United States Patent
Nakamura

(12) 
(10) Patent No.: US 12,377,002 B2
(45) Date of Patent: Aug. 5, 2025

(54) DISPOSABLE WEARING ARTICLE

(71) Applicant: Daio Paper Corporation, Ehime (JP)

(72) Inventor: Wataru Nakamura, Ehime (JP)

(73) Assignee: Daio Paper Corporation, Ehime (JP)

( * ) Notice: Subject to any disclaimer, the term of this patent is extended or adjusted under 35 U.S.C. 154(b) by 679 days.

(21) Appl. No.: 17/773,777

(22) PCT Filed: Nov. 18, 2020

(86) PCT No.: PCT/JP2020/043052
§ 371 (c)(1),
(2) Date: Oct. 18, 2022

(87) PCT Pub. No.: WO2021/100773
PCT Pub. Date: May 27, 2021

(65) Prior Publication Data
US 2023/0218450 A1 Jul. 13, 2023

(30) Foreign Application Priority Data
Nov. 20, 2019 (JP) ................................. 2019-209785

(51) Int. Cl.
*A61F 13/512* (2006.01)
*A61F 13/15* (2006.01)
*A61F 13/511* (2006.01)

(52) U.S. Cl.
CPC ...... *A61F 13/5126* (2013.01); *A61F 2013/15406* (2013.01); *A61F 2013/51117* (2013.01); *A61F 2013/5127* (2013.01)

(58) Field of Classification Search
CPC .......................... A61F 13/512; A61F 13/51113
See application file for complete search history.

(56) References Cited

U.S. PATENT DOCUMENTS 5,925,026 A * 7/1999 Arteman ........... A61F 13/53747
604/383
5,928,212 A * 7/1999 Kline ................ A61F 13/49009
604/386

(Continued)

FOREIGN PATENT DOCUMENTS

CN 1679455 10/2005
EP 0967949 1/2000

(Continued)

OTHER PUBLICATIONS

International Search Report for PCT/JP2020/043052, dated Feb. 2, 2021.

*Primary Examiner* — Jessica Arble
(74) *Attorney, Agent, or Firm* — Andrus Intellectual Property Law, LLP

(57) ABSTRACT

A disposable wearing article has a top sheet including a skin-contacting region which is in contact with skin of a wearer. The top sheet is a perforated nonwoven fabric having a hole-arranging area in which the holes penetrating a front surface of the perforated nonwoven fabric and a back surface thereof are arranged in a predetermined pattern. The skin-contacting region has a liquid-containing area containing a hydrophilic skin care liquid, the hole-arranging area, and an overlapping area in which the liquid-containing area and the hole-arranging area are overlapped each other. The top sheet is, at least at the entire hole-arranging area of the top sheet, bonded to an intermediate sheet or the like located at a back surface side of the top sheet with a hydrophobic hot melt adhesive.

13 Claims, 11 Drawing Sheets

(56) References Cited

U.S. PATENT DOCUMENTS

| | | | | |
|---|---|---|---|---|
| 6,498,284 B1* | 12/2002 | Roe | ............ | A61L 15/20 |
| | | | | 604/378 |
| 6,632,504 B1* | 10/2003 | Gillespie | ............ | D04H 3/14 |
| | | | | 442/352 |
| 6,716,441 B1* | 4/2004 | Osborne | ............ | A61L 15/46 |
| | | | | 424/404 |
| 2003/0050618 A1 | 3/2003 | Kondo et al. | | |
| 2005/0154362 A1 | 7/2005 | Warren et al. | | |
| 2010/0272483 A1 | 10/2010 | Nanjo | | |
| 2017/0165396 A1* | 6/2017 | Turner | ............ | A61F 13/514 |
| 2019/0000687 A1* | 1/2019 | Bianchi | ............ | A61F 13/51121 |
| 2019/0117473 A1* | 4/2019 | Rosati | ............ | A61F 13/515 |

FOREIGN PATENT DOCUMENTS

| | | |
|---|---|---|
| JP | 2002-509457 | 3/2002 |
| JP | 2010-526630 | 8/2010 |
| JP | 2014-940098 | 5/2014 |
| JP | 2017-217325 | 12/2017 |
| JP | 2018-102836 | 7/2018 |
| JP | 2019-170534 | 10/2019 |

* cited by examiner

[FIG.1]
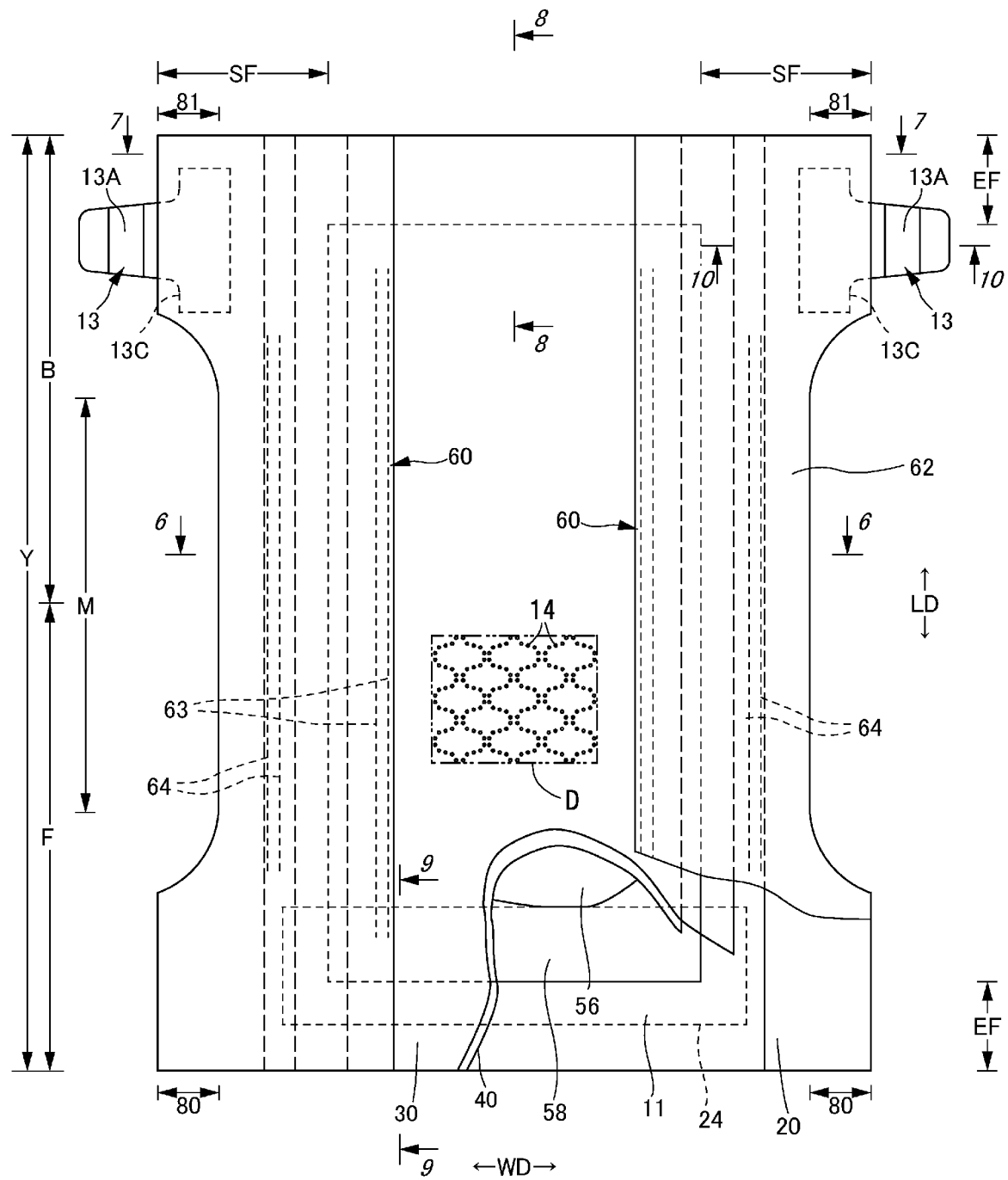

[FIG.2]
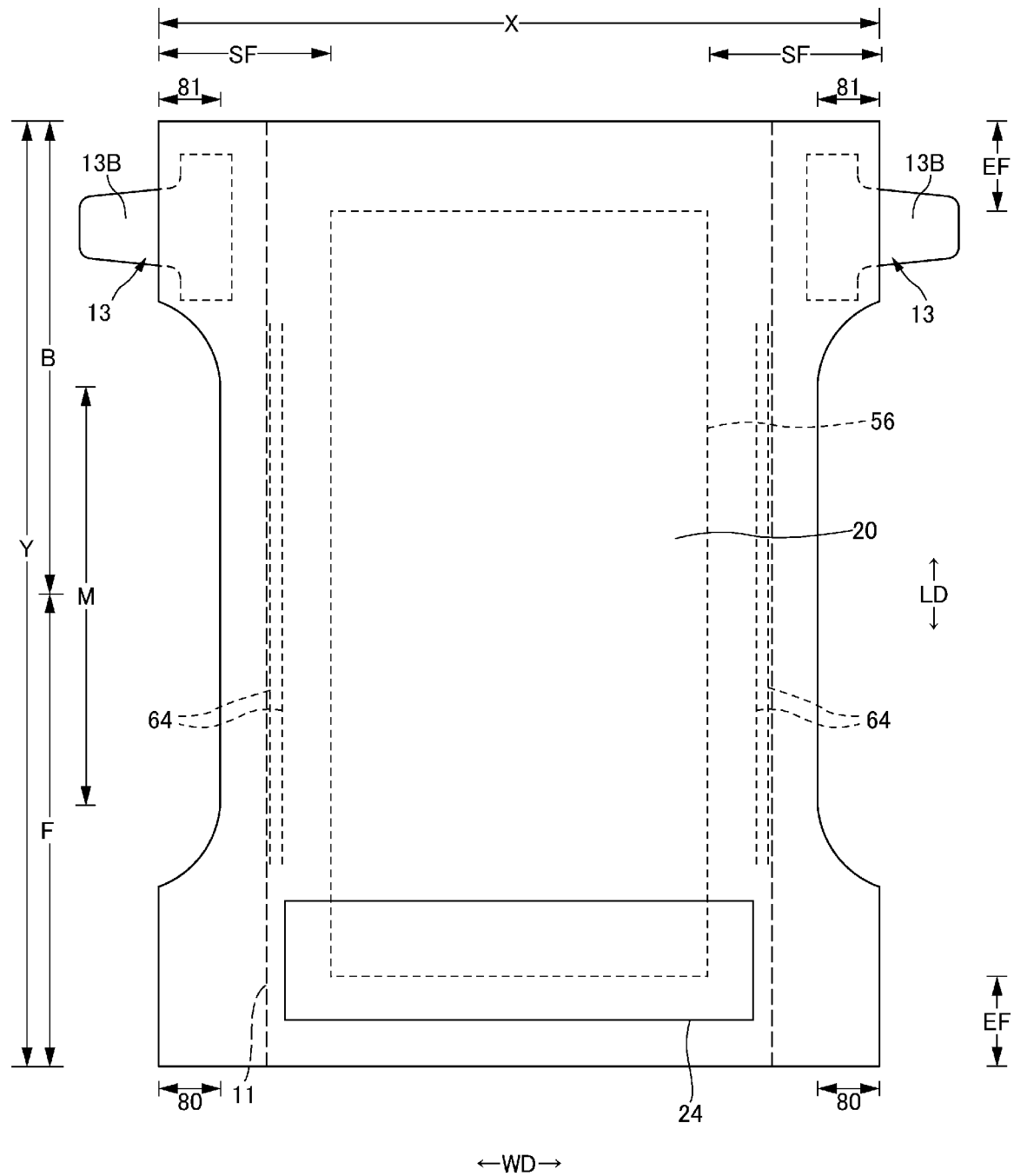

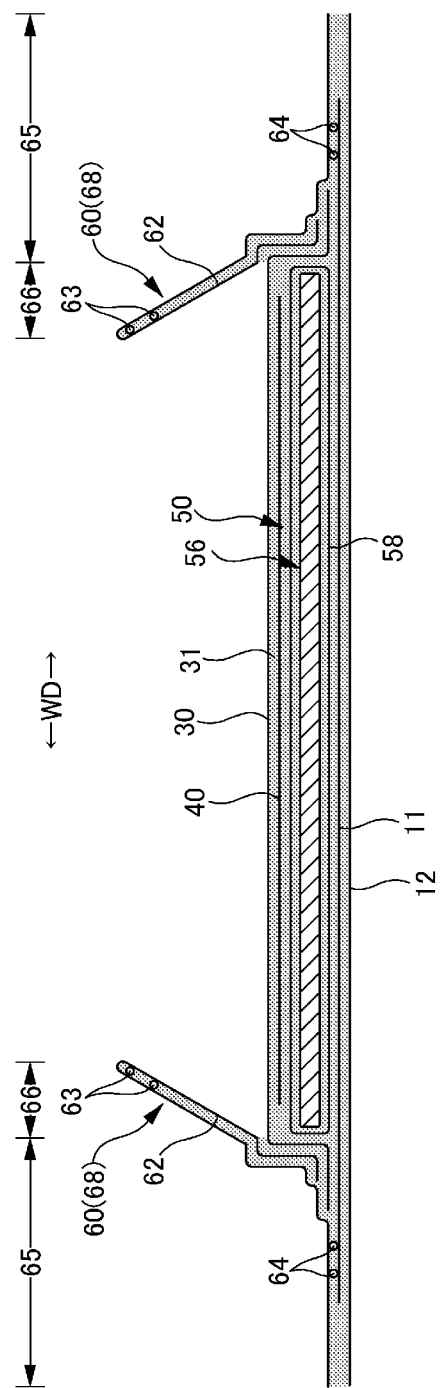

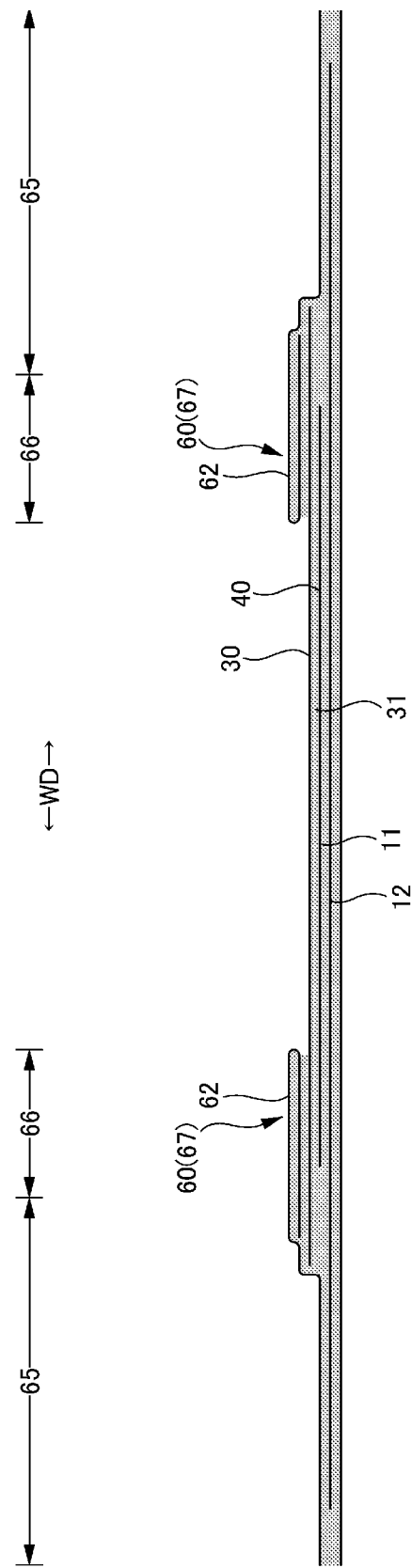
[FIG.4]

[FIG.5]
(a)
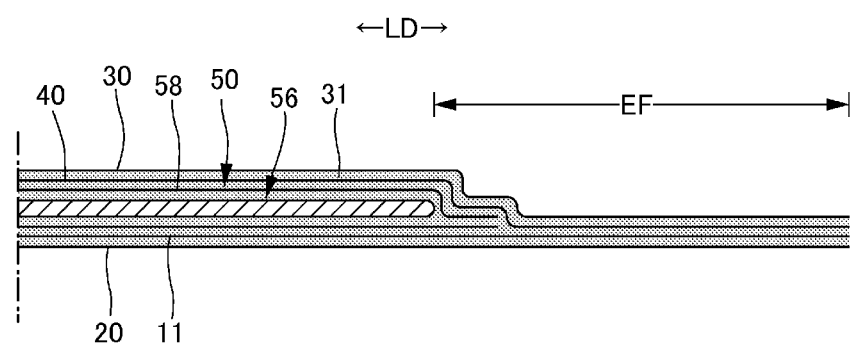
(b)
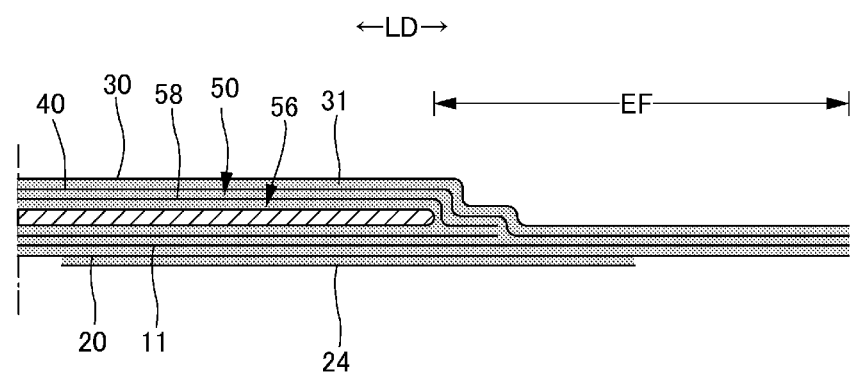
(c)
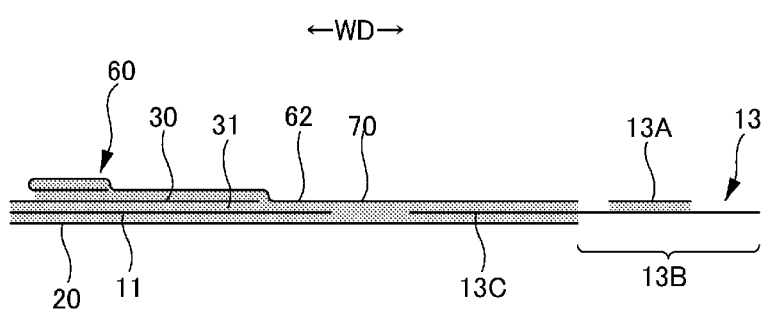

[FIG.6]
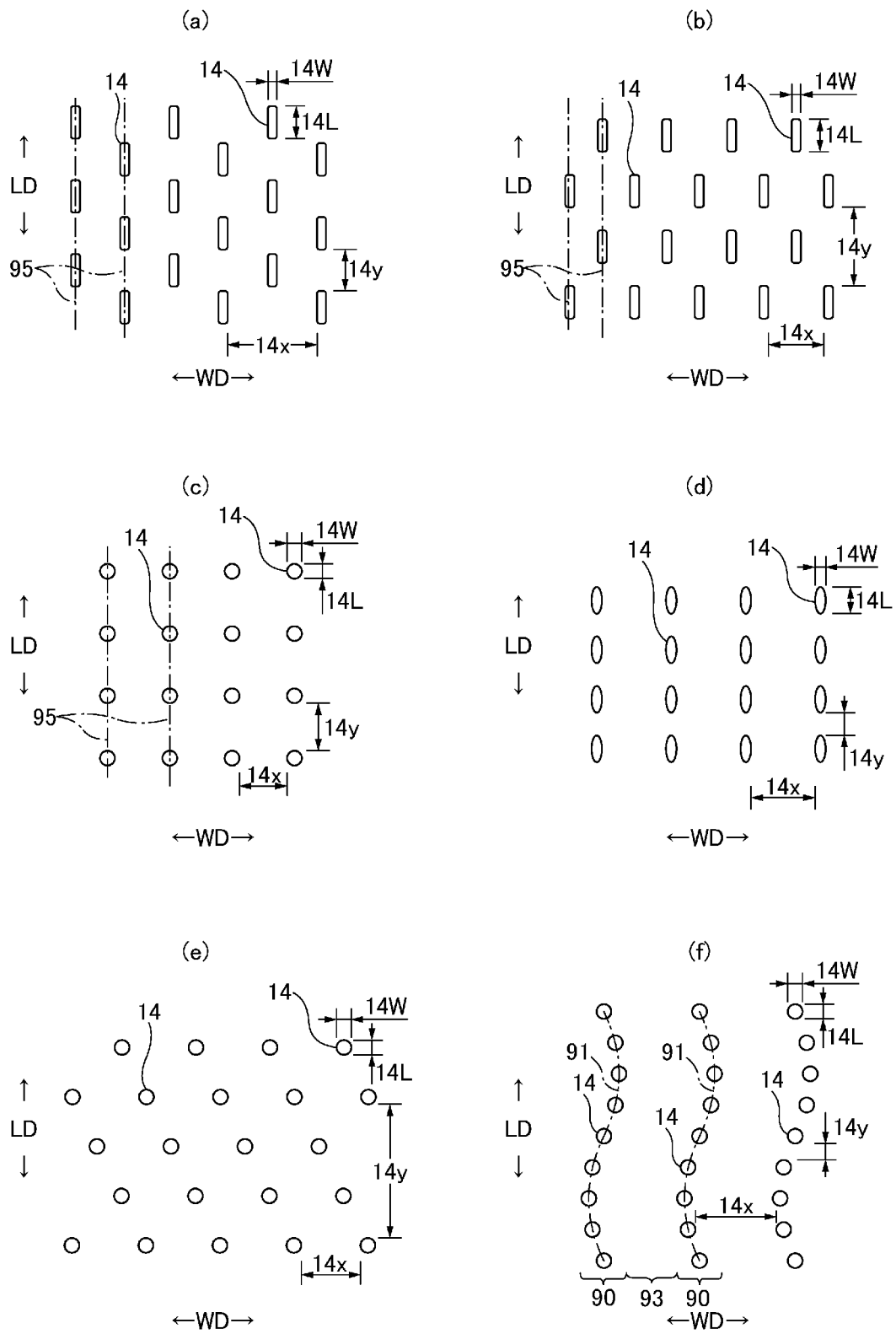

[FIG.7]
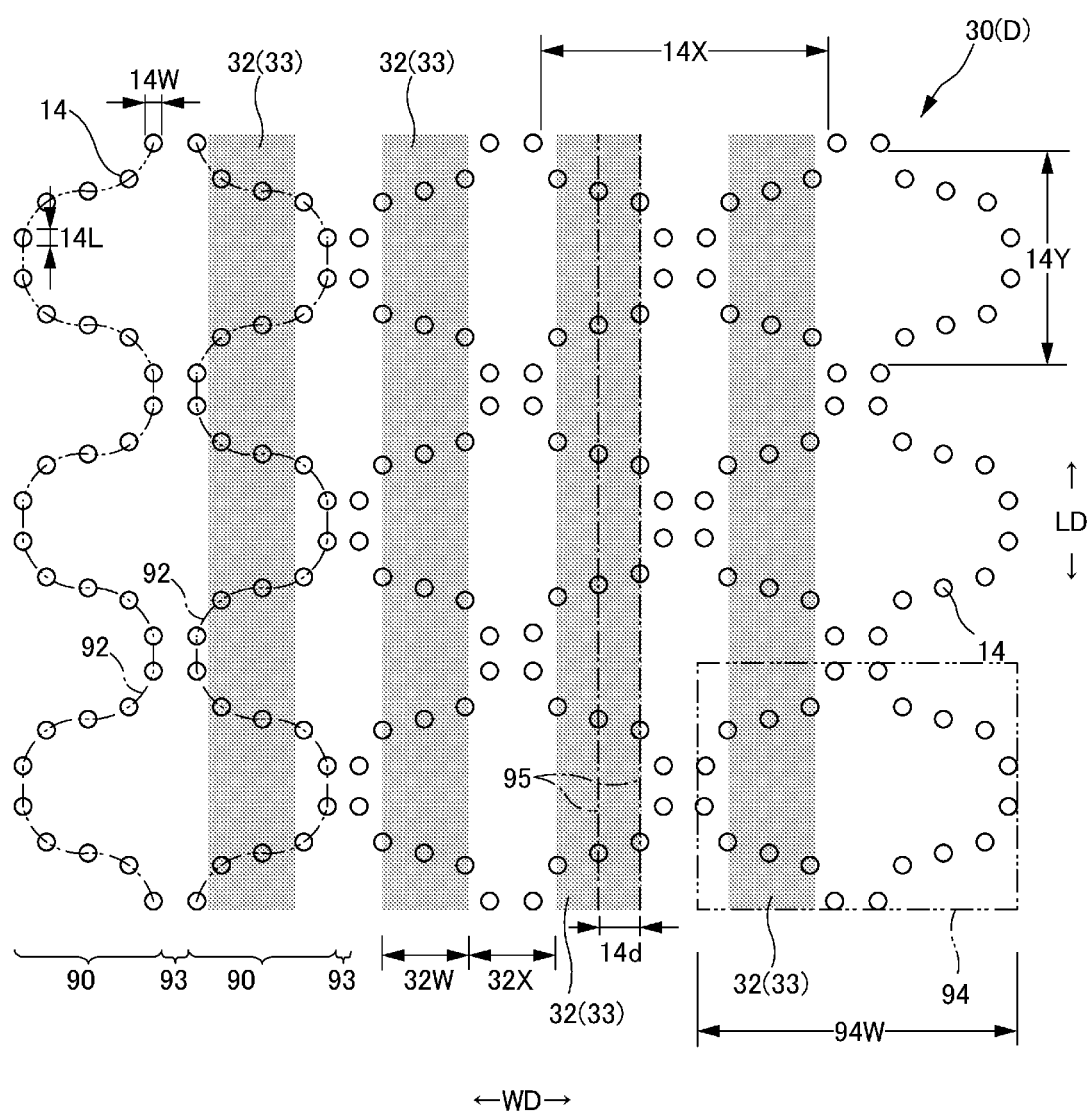

[FIG.8]
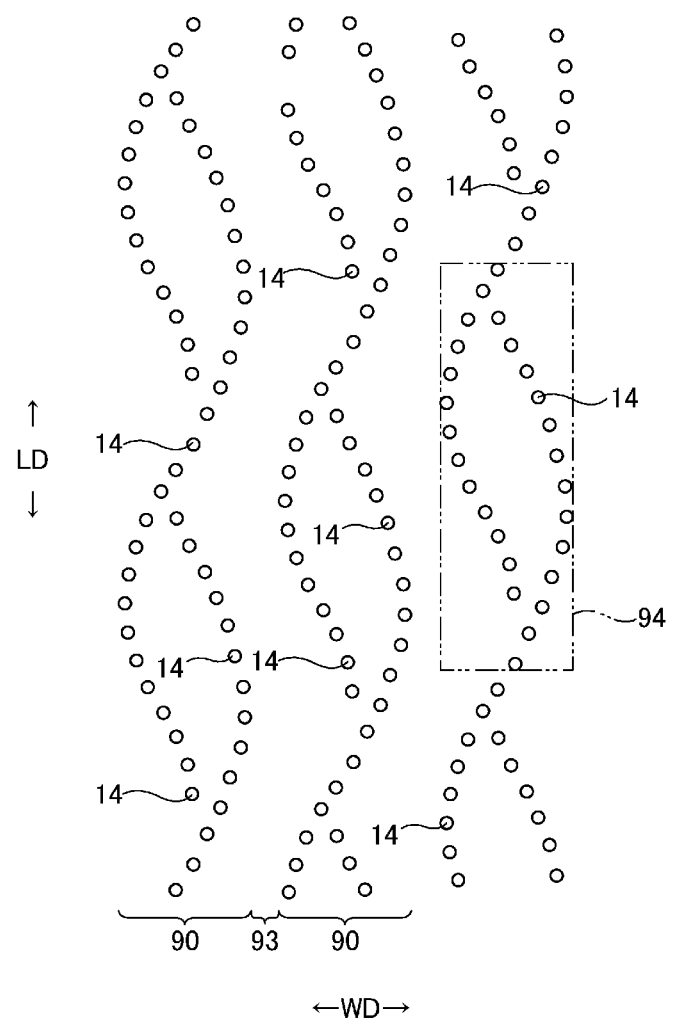

[FIG.9]
(a)
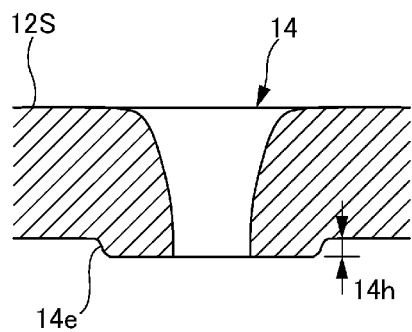
(b)
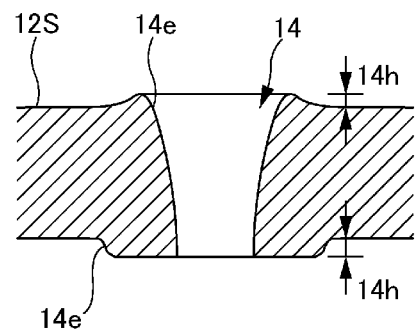
(c)
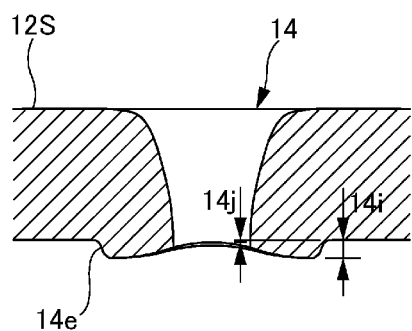
(d)
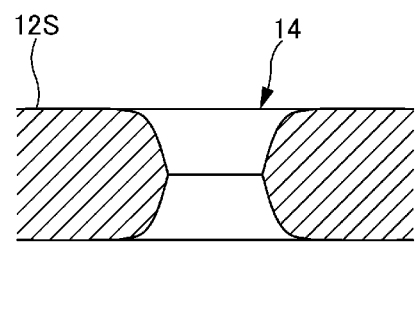

[FIG.10]
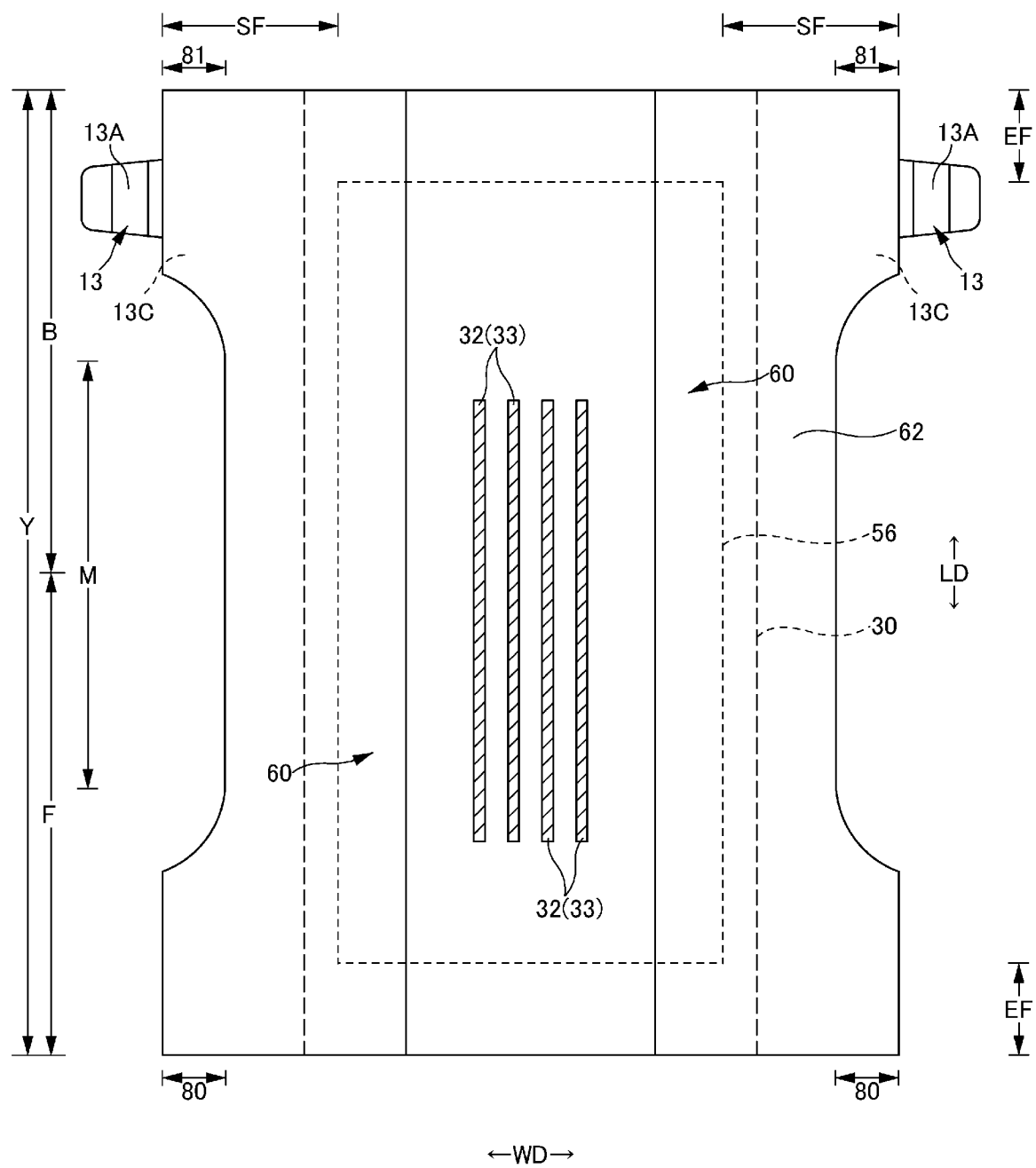

[FIG.11]
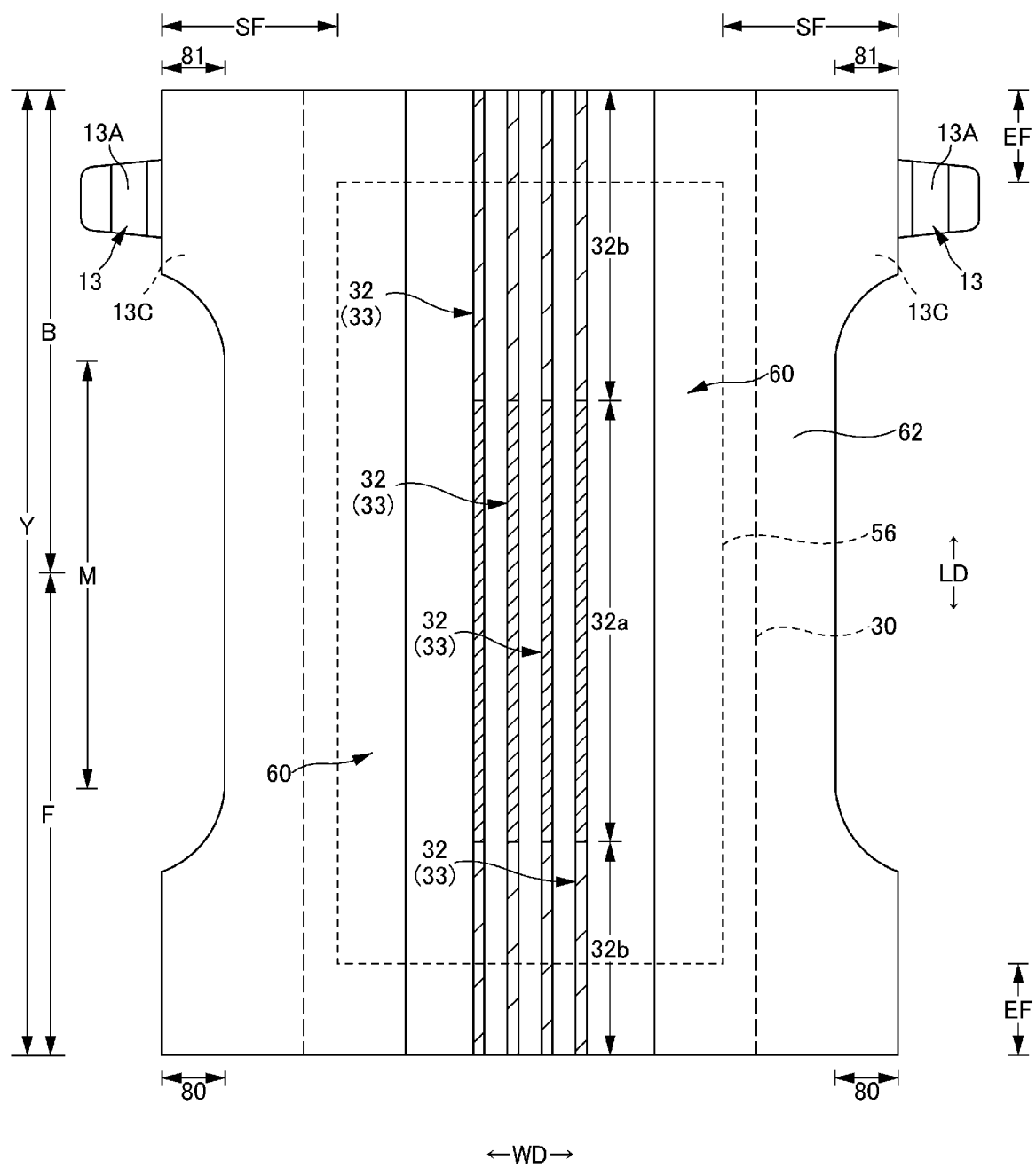

DISPOSABLE WEARING ARTICLE

CROSS-REFERENCE TO RELATED APPLICATIONS

This application is the U.S. national stage application of International Application PCT/JP2020/043052, filed Nov. 18, 2020, which international application was published on May 27, 2021, as International Publication WO 2021/100773 in the Japanese language. The International Application claims priority of Japanese Patent Application No. 2019-209785, filed Nov. 20, 2019. The international application and Japanese application are both incorporated herein by reference, in entirety.

TECHNICAL FIELD

The present invention relates to a disposable wearing article provided with a top sheet formed of a perforated nonwoven fabric.

BACKGROUND ART

In many disposable wearing articles such as disposable diapers and sanitary napkins, in order to obtain a cloth-like appearance and touch, a nonwoven fabric is used as a top sheet. As the nonwoven fabric, an imperforated nonwoven fabric is used which has no holes other than interfiber spaces, and in addition, a perforated nonwoven fabric is also used which is provided with many holes penetrating the front surface of the perforated nonwoven fabric and the back surface thereof (See Patent Literature 1).

Further, since the perforated nonwoven fabric can also be expected to impart functional beauty in improving air permeability and liquid permeability to the disposable wearing article, it is common to arrange the holes in a good-looking pattern in the fabric. For this reason, the visibility of the pattern of the holes (which means most of the holes is visible such that the whole pattern can be identified) is very important (as the visual effect). Accordingly, it is needless to say that the visibility of the individual holes is important.

Meanwhile, in recent years, due to growing needs for high-class products, there are articles in each of which a skin care agent is contained in a top sheet (See Patent Literatures 1 to 4)

However, when a skin care agent is contained in a top sheet formed of a perforated nonwoven fabric, a problem is caused that the visibility of the holes of the nonwoven fabric is partly deteriorated.

CITATION LIST

Patent Literature

Patent Literature 1: JP 2017-217325 A
Patent Literature 2: JP 2010-526630 A
Patent Literature 3: JP 2002-509457 A
Patent Literature 4: JP 2019-170534 A

SUMMARY OF INVENTION

Technical Problem

Therefore, a main object of the present invention is, for example, to inhibit, in a disposable wearing article provided with a top sheet formed of a perforated nonwoven fabric containing a skin care agent, the deterioration of visibility of the holes of the perforated nonwoven fabric.

Solution to Problem

The present inventor has obtained the following findings in research and development of a disposable wearing article in which a perforated nonwoven fabric containing a skin care agent is utilized as a top sheet. That is, one of factors that change visibility of the holes in a perforated nonwoven fabric is the change of a shape or an orientation of each hole of the perforated nonwoven fabric. For example, when the holes are collapsed by a force applied to the perforated nonwoven fabric, the visibility of the holes is deteriorated. In addition, it is needless to say that the visibility of the holes is improved as an angle of a user's visual line to a surface provided with the holes closes to a right angle. Then, when the angle of the user's visual line to a portion of the surface provided with the holes closes to 0 degree due to, for example, the formation of wrinkles on the portion, such a situation is, in appearance, the same as a situation in which the holes are collapsed, thus the visibility of the holes is deteriorated. When visibility of many holes is deteriorated in this way, the visibility of the whole pattern is deteriorated. In this case, even if a good-looking pattern is adopted, the good appearance thereof may be impaired.

A product of a disposable wearing article is in a plane state. However, when the disposable wearing article is put on, it should be deformed so as to fit the body surface.

Accordingly, it is impossible to prevent completely the formation of wrinkles on a top sheet. However, by fixing the entire top sheet to a back surface side member located on the back surface side of the top sheet, it is possible to prevent the corruption of the holes of the top sheet and the formation of unnecessary wrinkles on the top sheet. The top sheet is generally bonded to the back surface side member via a hydrophobic hot melt adhesive, which is applied on the back surface of the top sheet.

However, in this case, if an oil-soluble skin care liquid is contained in the top sheet, the adhesion of the top sheet with the hydrophobic hot melt adhesive is inhibited. Accordingly, the top sheet is partly peeled off from the back surface side member. Thus, in a portion of top sheet which is peeled off from the back surface side member in this way, the corruption of the holes of the top sheet are caused and the formation of wrinkles unnecessary for the top sheet are caused, resulting in the deterioration of visibility of the holes.

A disposable wearing article stated below is attained based on the above findings.
<First Aspect>

A disposable wearing article including a top sheet including a skin-contacting region which is in contact with skin of a wearer, wherein the top sheet is formed of a perforated nonwoven fabric having a hole-arranging area in which holes penetrating the perforated nonwoven fabric from front to back are arranged in a predetermined pattern, the skin-contacting region has a liquid-containing area containing a hydrophilic skin care liquid, the hole-arranging area, and an overlapping area in which the liquid-containing area and the hole-arranging area are overlapped each other, and the top sheet is, at least at the entire hole-arranging area of the top sheet, bonded to a back surface side member located at a back surface side of the top sheet with a hydrophobic hot melt adhesive.

(Function and Effect)

The present disposable wearing article is characterized in that the hydrophilic skin care liquid and the hydrophobic hot melt adhesive are combined. In a case where an oil-soluble skin care liquid is used, when the skin care liquid comes into contact with the hydrophobic hot melt adhesive in the overlapping area, adhesion with the hot melt adhesive is likely to be inhibited (and such inhibition includes reducing of bonding force and thereby interfacial peeling, in addition, also failure in bonding). On the other hand, in a case where the hydrophilic skin care liquid is used, when the skin care liquid comes into contact with the hydrophobic hot melt adhesive in the overlapping area, the adhesion with the hot melt adhesive is less likely to be inhibited. As a result, this makes it less likely that the top sheet is partly peeled off from the back surface side member. Thus, the corruption of the holes and the formation of the wrinkles, which would be caused in the peeled part of the top sheet, can be prevented, the visibility of the holes is therefore not less likely to be deteriorated.

<Second Aspect>

The disposable wearing article according to the first aspect, wherein the perforated nonwoven fabric has a fineness of 1 to 5 dtex and a basis weight of 10 to 30 $g/m^2$, the hydrophilic skin care liquid is a moisturizing agent containing glycerin as a main component, the liquid-containing area has a portion in which 5 to 15 $g/m^2$ of the hydrophilic skin care liquid per unit area is contained, and an application amount of the hydrophobic hot melt adhesive is 0.1 to 10 $g/m^2$.

(Function and Effect)

Although the type and the contained amount of the skin care liquid as well as the type and the application amount of the hot melt adhesive are not particularly limited, in a case where a common nonwoven fabric of the present aspect is used as the top sheet and the skin care liquid and the hot melt adhesive of the present aspect are used, it is preferable that the contained amount of the skin care liquid and the application amount of the hot melt adhesive are within the ranges of the present aspect.

<Third Aspect>

The disposable wearing article according to the first or second aspect, wherein a maximum dimension of the hole is 0.5 to 2 mm and an area rate of the holes in the hole-arranging area is 0.1 to 10%.

(Function and Effect)

In order to prevent the corruption of the holes and the formation of the wrinkles, the hot melt adhesive is preferably applied to the entire hole-arranging area, but by doing so, the applied hot melt adhesive possibly tends to overflow from the hole. To cope with this, it is useful to reduce the maximum dimension of the hole and reduce the number of the holes. However, in such a case, the visibility of the holes is likely to be deteriorated. Therefore, the above combination of the hydrophilic skin care liquid and the hydrophobic hot melt adhesive and the like bear significant meaning especially for the present aspect.

<Fourth Aspect>

The disposable wearing article according to any one of the first to third aspects, wherein in the pattern, rows of the holes aligned at intervals in a front-back direction are arranged at intervals in a width direction, the skin care liquid is applied in a stripe state, an application width of the skin care liquid is twice or less of a maximum value of a center-to-center interval of two rows of the holes adjacent to each other in the width direction, and an application interval of the skin care liquid is twice or more of the maximum value of the center-to-center interval of the two rows of the holes adjacent to each other in the width direction.

(Function and Effect)

Even if the combination of the hydrophilic skin care liquid and the hydrophobic hot melt adhesive is adopted, this does not make possible to prevent completely the inhibition of the adhesion of the hot melt adhesive. For example, in a case where the hydrophilic skin care liquid is applied to the top sheet and after that, the top sheet is bonded to the back surface side member with the hydrophobic hot melt adhesive, the adhesion of the hot melt adhesive is inhibited to some extent. On the other hand, when the arrangement of the applied skin care liquid has the above positional relation with respect to the pattern of the holes, even if the adhesion of the hot melt adhesive is inhibited such that the top sheet is partly peeled off, the number of the holes whose visibility might be deteriorated can be small, which is preferable.

<Fifth Aspect>

The disposable wearing article according to any one of the first to fourth aspects, wherein in the pattern, groups of the holes arranged in single-wavy lines or chained lines continuous in a front-back direction are arranged at intervals in a width direction, two groups of the holes adjacent to each other in the width direction are arranged in a same phase or different phases in the front-back direction, the skin care liquid is applied in a stripe state, an application width of the skin care liquid is one-third or less of a width of a unit arrangement portion in a group of the holes, and an application interval of the skin care liquid is one-third or more of the width of the unit arrangement portion in the group of the holes.

(Function and Effect)

Even if the combination of the hydrophilic skin care liquid and the hydrophobic hot melt adhesive is adopted, this does not make possible to prevent completely the inhibition of the adhesion of the hot melt adhesive. For example, in a case where the hydrophilic skin care liquid is applied to the top sheet and after that, the top sheet is bonded to the back surface side member with the hydrophobic hot melt adhesive, the adhesion of the hot melt adhesive is inhibited to some extent. On the other hand, when the arrangement of the skin care liquid has the above positional relation with respect to the pattern of the holes, even if the adhesion of the hot melt adhesive is inhibited such that the top sheet is partly peeled off, since this occurs only in a part of the unit arrangement portion, there is less likely to deteriorate visibility of the whole pattern, which is preferable.

<Sixth Aspect>

The disposable wearing article according to the fifth aspects, wherein the pattern is a Moroccan pattern.

(Function and Effect)

The arrangement pattern of the holes in the perforated nonwoven fabric is not particularly limited. However, in a case where the holes are arranged in a pattern having an aesthetical regularity as in this aspect, the visibility of the whole pattern becomes particularly important. Therefore, in the arrangement of the holes of the present aspect, the positional relation of the fifth aspect particularly bears significant meaning. A pattern in which two groups of the holes adjacent to each other in the width direction have phases opposite to each other is referred to as the Moroccan pattern (ogee pattern).

Advantageous Effects of Invention

It is an advantage brought by the present invention that in a disposable wearing article provided with a top sheet formed of a perforated nonwoven fabric containing a skin care agent, for example, it is possible to prevent the deterioration of visibility of the holes of the perforated nonwoven fabric.

BRIEF DESCRIPTION OF DRAWINGS

FIG. 1 is a plan view illustrating an inner surface of a tape-type disposable diaper in a spread state.
FIG. 2 is a plan view illustrating an outer surface of a tape-type disposable diaper in a spread state.
FIG. 3 is a cross-sectional view taken along line 6-6 in FIG. 1.
FIG. 4 is a cross-sectional view taken along line 7-7 in FIG. 1.
FIG. 5(a) is a cross-sectional view taken along line 8-8 in FIG. 1, FIG. 5(b) is a cross-sectional view taken along line 9-9 in FIG. 1, and FIG. 5(c) is a cross-sectional view taken along line 10-10 in FIG. 1.
FIGS. 6(a) to 6(f) are plan views illustrating various examples of arrangement patterns of holes.
FIG. 7 is a plan view illustrating an example of arrangement pattern (Moroccan pattern) of holes.
FIG. 8 is a plan view illustrating an example of arrangement pattern (chained pattern) of holes.
FIGS. 9(a) to 9(d) are cross-sectional views illustrating holes of perforated nonwoven fabrics.
FIG. 10 is a plan view illustrating an inner surface of a tape-type disposable diaper in a spread state.
FIG. 11 is a plan view illustrating an inner surface of a tape-type disposable diaper in a spread state.

DESCRIPTION OF EMBODIMENTS

FIGS. 1 to 5 illustrate an example of a tape-type disposable diaper. A reference sign X in the drawing designates the maximum width of the diaper excluding connecting tapes, and a reference sign L designates the maximum length of the diaper. In addition, a dotted pattern portion in each of cross-sectional views designates an adhesive as bonding means with which the constituent members are bonded to each other. The hot melt adhesive can be applied by a known method such as slot application, bead application into a continuous line or dot line, spray application into a spiral shape, a Z shape, or a wave shape, also by pattern coating (transfer of a hot melt adhesive by a letterpress method), or the like. Alternatively, the fixed portion of an elastic member is formed, instead of or in addition to the above applications of the hot melt adhesive, by an application of the hot melt adhesive to the outer peripheral surface of the elastic member, and the elastic member can be fixed to a member located adjacent thereto. Examples of the hot melt adhesive include an EVA-based agent, a pressure sensitive adhesive rubber-based agent (elastomer-based agent), a polyolefin-based agent, and a polyester/polyamide-based agent, and these can be used without particular limitation. As a bonding means for bonding the constituent members to each other, a means by material welding such as heat sealing or ultrasonic sealing also can be used.

Further, as a nonwoven fabric in the following description, a known nonwoven fabric can be appropriately used according to a site or a purpose. Examples of a constituent fiber of the nonwoven fabric include, but are not limited to, a synthetic fiber such as a polyolefin-based fiber including polyethylene and polypropylene, a polyester-based fiber, or a polyamide-based fiber (including a composite fiber such as core-sheath in addition to a single component fiber), a regenerated fiber such as rayon or cupra, and a natural fiber such as cotton. These fibers can be mixed and used. In order to enhance flexibility of the nonwoven fabric, it is preferable to use a crimped fiber as the constituent fiber. In addition, the constituent fiber of the nonwoven fabric may be a hydrophilic fiber (including a fiber that has become hydrophilic by a hydrophilizing agent), a hydrophobic fiber, or a water-repellent fiber (including a fiber that has become water-repellent by a water repellent agent). In addition, the nonwoven fabric is generally classified into a short fiber nonwoven fabric, a long fiber nonwoven fabric, a spunbond nonwoven fabric, a meltblown nonwoven fabric, a spunlace nonwoven fabric, a thermal bond (air-through) nonwoven fabric, a needle punch nonwoven fabric, a point bond nonwoven fabric, a laminated nonwoven fabric (an SMS nonwoven fabric, an SMMS nonwoven fabric, or the like in each of which different nonwoven fabric layers are laminated and a meltblown layer is sandwiched between spunbond layers, in addition to SSS nonwoven fabric in which same or similar nonwoven fabric layers are laminated), and the like depending on a fiber length, a sheet forming method, a fiber bonding method, and a stacked structure, and any of these nonwoven fabrics can be used. The laminated nonwoven fabric is manufactured as one unit including all layers integrally and refers to a fabric processed by bonding fibers across the all layers. However, the laminated nonwoven fabric does not include a fabric formed by sticking, with a hot melt adhesive or the like, a plurality of nonwoven fabrics which have been manufactured separately.

The present tape-type disposable diaper has a ventral side portion F extending forward from the center of a product in the front-back direction LD and a dorsal side portion B extending backward from the center of the product in the front-back direction LD. In addition, the present tape-type disposable diaper has, in terms of shape, a crotch portion M extending from the front side of the center of the product in the front-back direction to the back side of the center of the product in the front-back direction, front wings 80 disposed at positions of the front side apart from the center of the product in the front-back direction and protruded to both the right and left sides, respectively, and back wings 81 disposed at positions of the back side apart from the center of the product in the front-back direction and protruded to both the right and left sides. Further, the present tape-type disposable diaper includes an absorber 56 incorporated in a range including the crotch portion, a liquid pervious top sheet 30 covering the front surface side of the absorber 56, a liquid impervious sheet 11 covering the back surface side of the absorber 56, and an exterior nonwoven fabric 12 covering the back surface side of the liquid impervious sheet 11 and forming the outer surface of the product.

Hereinafter, a material and a characteristic part of each portion will be described in due order.
(Absorber)
The absorber 56 is a portion that absorbs and holds an excrement liquid and may be formed by an assembly of fibers. As this fiber assembly, in addition to one obtained by accumulating short fibers such as fluff pulps or synthetic fibers, a filament assembly obtained by opening a tow (fiber bundle) of synthetic fibers such as cellulose acetate as necessary can also be used. In a case where fluff pulps or short fibers are accumulated, a fiber basis weight may be, for example, about 100 to 300 g/m². In a case of a filament assembly, a fiber basis weight may be, for example, about 30 to 120 g/m². In a case of a synthetic fiber, a fineness is, for example, 1 to 16 dtex, preferably 1 to 10 dtex, and more preferably 1 to 5 dtex.

The planer shape of the absorber 56 may be appropriately determined, and may be a rectangular shape, or may be a narrowing shape whose both side edges each being narrowed along a periphery of a leg in an intermediate part in the front-back direction LD of the absorber 56.

(Super Absorbent Polymer Particles)

The absorber 56 may partially or entirely contain super absorbent polymer particles. The super absorbent polymer particles include "powder" in addition to "particles". As the super absorbent polymer particles, those used for this type of absorbent article can be used as they are. The particle diameters of the super absorbent polymer particles are not particularly limited. However, for example, when sieving using a standard sieve of 500 µm (JIS Z8801-1: 2006) (shake for five minutes) is performed, and particles falling under the sieve using this sieving are sieved using a standard sieve of 180 µm (JIS Z8801-1: 2006) (shake for five minutes), it is desirable that a ratio of particles remaining on the standard sieve of 500 µm is 30% by weight or less, and a ratio of particles remaining on the standard sieve of 180 µm is 60% by weight or more.

A material of the super absorbent polymer particles can be used without particular limitation, but those having a water absorption capacity of 40 g/g or more are preferable. Examples of the super absorbent polymer particles include a starch-based material, a cellulose-based material, and a synthetic polymer-based material. A starch-acrylic acid (salt) graft copolymer, a saponified product of a starch-acrylonitrile copolymer, a cross-linked product of sodium carboxymethyl cellulose, an acrylic acid (salt) polymer, or the like can be used. As the shapes of the super absorbent polymer particles, a usually used particulate material shape is suitable, but other shapes also can be used.

As the super absorbent polymer particles, those having a water absorption rate of 70 seconds or less, particularly of 40 seconds or less are suitably used. When the water absorption rate is too slow, so-called returning that a liquid supplied into the absorber 56 returns out of the absorber 56 tends to occur.

As the super absorbent polymer particles, those having a gel strength of 1000 Pa or more are suitably used. This makes it possible to effectively suppress feeling of stickiness after liquid absorption even in a case of using a bulky absorber 56.

The basis weight of the super absorbent polymer particles can be appropriately determined depending on the absorption amount required for the usage of the absorber 56. Thus, although it is not necessarily appropriate to suggest, the basis weight may be, in a usual case, within the range of 50 to 350 g/m².

(Wrapping Sheet)

The absorber 56 can be incorporated as an absorbent element 50 wrapped in a wrapping sheet 58 in order to prevent escape of the super absorbent polymer particles or to improve shape maintenance of the absorber 56. As the wrapping sheet 58, tissue paper, particularly crepe paper, a nonwoven fabric, a polyethylene laminated nonwoven fabric, a perforated sheet, or the like can be used. However, it is desirable that the wrapping sheet 58 is a sheet from which super absorbent polymer particles do not escape. When a nonwoven fabric is used instead of crepe paper, a hydrophilic spunbond/meltblown/meltblown/spunbond (SMMS) nonwoven fabric is particularly suitable, and polypropylene, polyethylene/polypropylene, or the like can be used as a material thereof. A nonwoven fabric having a fiber basis weight of 5 to 40 g/m², particularly of 10 to 30 g/m² is desirable.

As illustrated in FIG. 3, the single wrapping sheet 58 may wrap the whole of the absorber 56. In addition to this wrapping manner, a plurality of the wrapping sheets 58 such as upper and lower two wrapping sheets 58 may wrap the whole of the absorber 56. The wrapping sheet 58 can be omitted.

(Top Sheet)

The top sheet 30 extends from the front end to the back end of the product in the front-back direction and extends to the lateral sides beyond the absorber 56 in the width direction WD. However, for example, when lines, from which rising gathers 60 described later start to rise, are closer to the center in the width direction than the side edges of the absorber 56, appropriate deformation can be made, for example, the width of the top sheet 30 is made shorter than the maximum width of the absorber 56 as necessary.

The top sheet 30 includes a skin-contacting region which is in contact with skin of a wearer. In addition, it is preferable that the top sheet 30 is a perforated nonwoven fabric having a hole-arranging area in which holes 14 penetrating a front surface of the perforated nonwoven fabric and a back surface thereof are arranged in a predetermined pattern. The shapes, dimensions, arrangement patterns and the like of the holes 14 can be appropriately determined. In order to make FIG. 1 easier to understand, the holes 14 are shown only in a single portion D in this drawing, but this portion D does not refer to the hole-arranging area.

The type of the perforated nonwoven fabric is not particularly limited, but a short fiber nonwoven fabric such as an air-through nonwoven fabric is preferable from a viewpoint of flexibility. The fineness is preferably about 1 to 5 dtex, and more preferably 1 to 3 dtex and the basis weight is preferably about 10 to 30 g/m².

The hole-arranging area can be disposed only in a middle area in the front-back direction LD of the top sheet 30, or only in a middle area in the width direction WD of the top sheet 30 (these middle areas may partly include portions having no holes 14.) Alternatively, the entire top sheet 30 can be used as the hole-arranging area. Namely, as long as the hole-arranging area is provided in the skin-contacting region, this area can extend beyond the skin-contacting region (for example, this area can extend to sites to which gather sheets 82 are bonded in the both sides in the width direction WD).

A planar shape (opening shape) of each hole 14 can be appropriately determined. It can have an arbitrary shape such as an elongated hole shape as illustrated in FIGS. 6(*a*) and 6(*b*), a perfect circle as illustrated in FIGS. 6(*c*), 6(*e*), 6(*f*), 7 and 8, an ellipse as illustrated in FIG. 6(*d*), a polygon such as a triangle, a rectangle, and a rhombus, a star shape, a cloud shape, etc. Although not shown, different kinds of shapes may coexist. The dimensions of the individual holes 14 are not particularly limited, but the dimension in the front-back direction (maximum dimension in the front-back direction) 14L is preferably is 0.5 to 2.0 mm, particularly preferably 0.5 to 2.0 mm, and the width direction dimension (the maximum dimension in the width direction) 14W is preferably 0.5 to 2.0 mm, particularly preferably 0.5 to 1.0 mm. In the case where the shape of the hole 14 is long in the front-back direction (a shape having a maximum length in one direction longer than a length in the direction orthogonal thereto) like an elongated hole shape, an ellipse, a rectangle, and a rhombus, the maximum dimension in the front-back direction is preferably 1.2 to 2.5 times the maximum dimension in the direction orthogonal thereto. Further, when the shape of the hole 14 is long in one direction, it is desirable that the longitudinal direction of the hole 14 be the machine direction (MD) of the nonwoven fabric, but it may be cross direction (CD) or the slanting direction oblique to these directions. In many cases, the machine direction (MD) of the perforated nonwoven fabric constituting the top sheet 30 is identical to the front-back direction LD.

An area and an area rate of the individual holes 14 in the hole-arranging area may be appropriately determined, but the area is preferably about 0.25 to 4.00 mm², and the area rate is about 0.1 to 10.0%.

The arrangement pattern of the holes 14 can be appropriately determined. For example, the arrangement pattern is preferably a matrix shape in which rows of the holes 14 arranged linearly at predetermined intervals in the front-back direction LD are repeated at predetermined intervals in the width direction WD as illustrated in FIGS. 6(*a*), 6(*c*) and 6(*d*). In this case, as illustrated in FIGS. 6(*a*) and 6(*d*), an interval 14*y* of the holes 14 in the front-back direction LD may be shorter than an interval 14*x* of the holes 14 in the width direction WD. In addition, as illustrated in FIG. 6(*c*), the interval 14*y* of the holes 14 in the front-back direction LD may be substantially the same as the interval 14*x* of the holes 14 in the width direction WD, or as illustrated in FIGS. 6(*b*) and 6(*e*), the interval 14*y* of the holes 14 in the front-back direction LD may be longer than the interval 14*x* of the holes 14 in the width direction WD. Further, as illustrated in FIGS. 6 (*b*) and 6(*e*), the rows 95 of the holes arranged linearly at predetermined intervals in the front-back direction LD can be arranged at intervals in the width direction with positional deviation of the holes in the rows 95 in the front-back direction LD. In the examples illustrated in FIGS. 6(*a*) and 6(*b*), the positions of the holes 14 in two rows 95 adjacent to each other are deviated alternately so as to form staggered shapes (hexagonal lattice shapes).

An interval 14*y* of the holes 14 in the front-back direction and an interval 14*x* of the holes in the width direction may be constant or may be changed. These can be appropriately determined, but for example, an interval 14*y* of the holes 14 in the front-back direction can be 0.9 to 8.0 mm, particularly 1.0 to 3.0 mm, and an interval 14*x* of the holes 14 in the width direction can be 2.0 to 10 mm, particularly 3.0 to 5.0 mm.

In addition, as shown in FIGS. 6(*f*) and 7, in arrangement patterns of the holes 14, groups 90 of the holes 14 arranged in the front-back direction LD in single-wavy lines 91, 92 are arranged at intervals in the width direction WD in a same phase or different phases. In a pattern of an example illustrated in FIG. 7, two groups 90 of the holes 14 adjacent to each other in the width direction WD are arranged in phases opposite to each other such that virtual lines each connecting the holes 14 show a Moroccan pattern (ogee pattern). Further, as shown in FIG. 8, groups 90 of the holes 14 aligned in chained lines continuous in the front-back direction LD can be arranged at intervals in the width direction WD. Here, "groups 90 of the holes 14 - - - be arranged at intervals in the width direction WD" means that a hole-less portion 93 continuous in a straight line along the front-back direction LD is disposed between the two groups 90 of the holes 14 adjacent to each other in the width direction WD.

The sectional shape of the hole 14 is not particularly limited. For example, the hole 14 may be a punched type whose peripheral edge is formed with cut ends of fibers, or a non-punched type whose peripheral edge has almost no cut ends of fibers and is formed by inserting and pushing a pin among the fibers (to have a higher density of fibers at an edge portion). In the punched type of hole, as shown in FIG. 9(*d*), the diameter of the hole 14 may decrease as it approaches the middle in the thickness direction, or although not shown, the diameter of the hole 14 may decrease as it approaches one side in the thickness direction.

In the non-punched type of hole 14, the diameter of the hole 14 decreases as it approaches from a pin-inserting side toward an opposite side thereto. This type of hole includes a hole 14 whose diameter continues to decrease throughout across the nonwoven fabric layer in the thickness direction, and also a hole 14 whose diameter continues to decrease to the middle in the thickness direction and after that whose diameter does not substantially decrease any more. Such non-punched type of hole includes a hole 14 whose edge portion at an opposite side to a pin-inserting side has a protruding portion (burr) 14*e* formed by pushing fibers outward to the opposite side to the pin-inserting side provided with no protruding portion 14*e* as illustrated in FIGS. 9(*a*) and 9(*c*). Further, the non-punched type of hole includes also a hole 14 whose edge portion at an opposite side to a pin-inserting side has a protruding portion 14*e* formed by pushing fibers outward to the opposite side to the pin-inserting side and whose edge portion at the pin-inserting side has a protruding portion 14*e* formed by pushing fibers outward to the pin-inserting side as illustrated in FIG. 9(*b*). In addition, the former non-punched type of hole includes a hole 14 whose protruding portion 14*e* has a substantially uniform height 14*h* as shown in FIG. 9(*a*), and includes also a hole 14 whose protruding portion 14*e* has a highest opposing portion having the highest protruding height 14*i* and a lowest opposing portion being orthogonal in the opposing direction to the highest opposing portion and having the lowest protruding height 14*j* as shown in FIG. 9(*c*). It is preferable that the protruding portion 14*e* is continuous in the peripheral direction of the hole to form a cylindrical shape. However, in some holes 14 among the holes or in all of the holes 14, each protruding portion 14*e* may be formed at a part of periphery of the hole 14 in the peripheral direction thereof. It is preferable that the protruding heights 14*h*, 14*i*, 14*j* (the apparent height measured by using an optical microscope in a state where a pressure is not applied) be about 0.2 to 1.2 mm. Further, in the protruding portion 14*e*, the highest protruding height 14*i* is preferably about 1.1 to 1.4 times the lowest protruding height 14*j*. The protruding height of the protruding portion 14*e* may change along the peripheral direction.

For example, as illustrated in FIGS. 6(*a*), 6(*b*) and 6(*d*), when the hole 14 having a long dimension in one direction is formed by inserting a pin, the fibers in the edge portion of the hole 14 are retracted outside or in a vertical direction, the protruding portion (burr) 14*e* of the hole 14 is formed, and the protruding height 14*i* of the opposing portion in the longitudinal direction of the hole 14 is higher than the protruding height 14*j* of the opposing portion being orthogonal in the opposing direction to the longitudinal direction. The protruding portion 14*e* of the hole 14 may have a lower density of the fibers than those of surroundings, but it is preferable that it be equal to or higher than those of the surroundings.

Particularly, it is preferable that the hole 14 is formed by inserting a pin to a long fiber nonwoven fabric having a fineness of 0.1 to 5.0 dtex (more preferably, 1.0 to 3.0 dtex), a basis weight of 15 to 20 g/m² (more preferably, 15 to 18 g/m²) and a thickness of 0.3 to 0.8 mm (more preferably, 0.3 to 0.6 mm) as the perforated nonwoven fabric, because the height of the protruding portion 14e formed at the edge portion of the hole 14 becomes low. More specifically, in a case where the perforated nonwoven fabric is the long fiber nonwoven fabric having the above specific ranges, when the hole is formed by inserting the pin, the fibers are less likely to be extruded in the thickness direction. This is because, the fibers to which a force is applied by the inserted pin are continuous (continuous fibers) while they are tangled each other over the entire surface of the nonwoven fabric such that movements of the fibers in a portion to which the force is applied by the inserted pin are suppressed by a portion continuous from the above portion. In addition, the long fiber nonwoven fabric having the above specific ranges has basically a fiber density being appropriately low such that the fibers can move relatively easily in a direction orthogonal to the thickness direction. Then, if the pin is inserted to the long fiber nonwoven fabric having the above specific ranges and the hole 14 having the above specific ranges of dimensions is formed, when the pin is inserted, the fibers near the pin move toward an outlet for the pin while they are extruded in a radial manner from the direction along which the pin is inserted as a center. As a result, although the protruding portion 14e is formed, the height thereof becomes low. Further, for this reason, in the edge portion of the hole 14, a high density portion in which the fiber density is higher than the surroundings is formed. Due to this high density portion, shade of the hole becomes deeper with respect to the periphery of the hole, resulting in improved visibility of the hole, which is an advantage.

(Intermediate Sheet)

In order to quickly transfer the liquid that has passed through the top sheet 30 to the absorber, it is possible to dispose an intermediate sheet (also referred to as "second sheet") 40 having a higher liquid transmission rate than that of the top sheet 30. The intermediate sheet 40 is used in order to rapidly transfer a liquid to the absorber to enhance absorption performance by the absorber, and to preventing a "returning" phenomenon of the absorbed liquid from the absorber. The intermediate sheet 40 can also be omitted.

As the intermediate sheet 40, a liquid permeable sheet such as a nonwoven fabric can be used. As the intermediate sheet 40, particularly, an air-through nonwoven fabric is preferable because of being bulky. As the air-through nonwoven fabric, a composite fiber having a core-sheath structure is preferably used. In this case, a resin used for the core may be polypropylene (PP) but is preferably polyester (PET) having high rigidity. The basis weight is preferably 17 to 80 g/m², and more preferably 18 to 60 g/m². A constituent fiber of the nonwoven fabric preferably has a fineness of 2.0 to 10 dtex. In order to make the nonwoven fabric bulky, as all of constituent fibers or some of mixed fibers, eccentric fibers having no core in the center, hollow fibers, eccentric and hollow fibers are also preferably used.

The intermediate sheet 40 in the illustrated example is disposed at the center in the width direction so as to be shorter than the width of the absorber 56, but may be disposed over the maximum width. The intermediate sheet 40 may be disposed over the maximum length of the diaper, but may be disposed only in a middle portion in the front-back direction LD including an excrement position as in the illustrated example.

(Liquid Impervious Sheet)

Although the liquid impervious sheet 11 is not particularly limited, it has preferably moisture perviousness. As the liquid impervious sheet 11, for example, a microporous sheet can be used preferably which is obtained by kneading an inorganic filler in a polyolefin-based resin such as polyethylene or polypropylene, molding the kneaded mixture into a sheet, and stretching the sheet in one or two axial directions. Furthermore, the liquid impervious sheet 11 can be used which has a nonwoven fabric as a base material to enhance waterproof property.

It is desirable that the liquid impervious sheet 11 extends within the same range as or a wider range than that of the absorber 56 in the front-back direction LD and the width direction WD. However, for example, when another water blocking means is present, as another possible configuration, the end portion of the absorber 56 does not have to be covered with the liquid impervious sheet 11 in the front-back direction LD or the width direction WD as necessary.

(Exterior Nonwoven Fabric)

The exterior nonwoven fabric 12 covers the entire back surface side of the liquid impervious sheet 11 and imparts a cloth-like appearance to the outer surface of the product. The fiber basis weight of the exterior nonwoven fabric 12 is preferably 10 to 50 g/m², particularly 15 to 30 g/m², but is not limited thereto. The exterior nonwoven fabric 12 can be omitted, and in this case, the liquid impervious sheet 11 can extend to the side edges of the product.

(Rising Gather)

In order to block excrement that moves laterally on the top sheet 30 and to prevent so-called side leakage, the rising gathers 60 rising toward the skin side of the wearer are preferably disposed on the both sides of a surface of the top sheet 30 in the width direction WD. It is needless to say that the rising gather 60 can be omitted.

When the rising gather 60 is adopted, a structure thereof is not particularly limited, and any of known structures can be adopted. The rising gather 60 in the illustrated example includes the gather sheet 62 substantially continuous in the width direction WD, and an elongated gather elastic member 63 fixed to the gather sheet 62 in a stretched state along the front-back direction LD. A water repellent nonwoven fabric can be used as the gather sheet 62, and a rubber thread or the like can be used as the gather elastic member 63. In addition to providing a plurality of elastic members for each side as illustrated in FIGS. 1 and 2, it is also possible to provide a single elastic member for each side.

The inner surface of the gather sheet 62 has a bonding start part in the width direction WD on the side portion of the top sheet 30. A portion extending outwardly in the width direction from the bonding start part is bonded to the inner surface of each side flap part SF, that is, in the illustrated example, bonded to the side portion of the liquid impervious sheet 11 and the side portion of the exterior nonwoven fabric 12 located in the outer side thereof in the width direction with a hot melt adhesive or the like.

In an around-leg portion, the inner side of the bonding start part of the rising gather 60 in the width direction WD is fixed to the top sheet 30 at both end portions in a product front-back direction. However, a portion therebetween is a non-fixed free portion, and the free portion rises by a contraction force of the elastic member 63 and comes into close contact with a body surface.

(End Flap Part, Side Flap Part)

The tape-type disposable diaper in the illustrated example has a pair of end flap parts EF without the absorber 56 and extending outwardly to the front side and the back side of the absorber 56 respectively, and a pair of side flap parts SF without the absorber 56 and extending outwardly in the lateral side beyond the both side edges of the absorber 56 respectively. The side flap part SF may be formed of a main sheet (the exterior nonwoven fabric 12, and the like) continuous from a portion including the absorber 56 as shown in the illustrated example, or may be formed by attaching another material.

(Plane Gather)

To each side flap part SF, a side elastic member 64, which is an elongated elastic member formed of rubber thread or the like, is fixed in a stretched state along the front-back direction LD, hence an around-leg portion in each side flap part SF is configured as a plane gather. The side elastic members 64 can be disposed between the liquid impervious sheet 11 and the exterior nonwoven fabric 12 in the side flap part SF, in addition to between the gather sheet 62 and the liquid impervious sheet 11 in an outer side in the width direction in the vicinity of the bonding start part in a bonded portion of the gather sheet 62 as in the illustrated example. A plurality of the side elastic members 64 may be disposed on each side as in the illustrated example, or only one side elastic member 64 may be disposed on each side.

The plane gather is a portion to which a contraction force of the side elastic member 64 is applied (a portion in which the side elastic members 64 are illustrated in the drawings). Thus, in addition to a configuration in which the side elastic members 64 are present only in a site of the plane gather, there may be other configurations. In each of these other configurations, the side elastic members 64 are present in a range from the plane gather to a front side, to a back side, or to both the front and back sides of the plane gather. However, in other sites than the plane gather, the side elastic members 64 are finely cut at one place or at many places; the side elastic members 64 are not fixed to sheets sandwiching the side elastic members 64; or both the above two measures are carried out. As a result, the contraction force is not applied to the other sites than the plane gather (which is substantially equivalent to that the elastic members are not provided on the other sites) such that the contraction force of the side elastic members 64 is applied only to the site of the plane gather.

(Front Wing)

The present tape-type disposable diaper has front wings 80 protruding to both the right and left sides at positions separated from the center in the front-back direction of the product in the front side thereof. The front wing can be omitted (namely, the product has a shape whose width is not changed from a portion having the smallest width to the front end of the product.)

The dimension in the width direction WD of the front wing 80 can be appropriately determined, but for example, may be 5 to 20% (particularly 7 to 15%) of the maximum length L of the article. The dimension in the width direction WD of the front wing 80 can be the same as the dimension in the width direction WD of a back wing 81 described later.

(Back Wing)

The present tape-type disposable diaper has back wings 81 protruding to both the right and left sides at positions separated from the center in the front-back direction of the product in the back side thereof.

The dimension in the width direction WD of the back wing 81 can be appropriately determined. It can be the same as the dimension in the width direction WD of the front wing 80. In addition, it can be smaller or larger than the dimension in the width direction of the front wing 80.

(Intermediate Part)

Each side edge 15 of the product disposed between the front wing 80 and the back wing 81 may have a substantially straight line shaped part passing within a range having the width of ±5 mm in a direction orthogonal to a line as a center having an acute intersecting angle of less than ±2 degrees with respect to the front-back direction LD. Each side edge 15 disposed between the front wing 80 and the back wing 81 may have a wavy shape or an arched shape (not shown) or may have a straight line shape as in the illustrated example.

(Formation of Wing)

As shown in the illustrated example, in each side portion of the product, an entire part of an edge having a depressed shape can be formed throughout from a lower edge of the front wing 80 to a lower edge of the back wing 81 through a side edge 15 between the front wing 80 and the back wing 81 by cutting and removing the side portion of the side flap SF into the depressed shape. In this case, the laminated structure of the front wing 80 and the laminated structure of the back wing 81 are determined by the laminated structure of the side flap SF, and in the illustrated example, the front wing 80 and the back wing 81 are formed with the gather sheet 62 and the exterior nonwoven fabric 12. Although not shown, a front extended sheet protruding laterally from the side flap SF is provided such that the entire part of the front wing 80 or a portion of a tip part of the front wing 80 can be formed with the front extended sheet. Similarly, a back extended sheet protruding laterally from the side flap SF is provided such that the entire part of the back wing 81 or a portion of the tip part of the back wing 81 can be formed with the back extended sheet. As the front extended sheet and the back extended sheet, various kinds of nonwoven fabrics can be used.

(Connecting Portion)

In the back wing 81, a connecting portion 13A is provided which is to be detachably connected to the ventral side portion F for wearing the diaper. That is, when the diaper is put on, both the side portions of the back wings 81 are taken to the ventral side of the wearer, and the connecting portions 13A are connected to the outer surface of the ventral side portion F. As the connecting portion 13A, a hook material (male member) of a mechanical fastener (hook and loop fastener) or an adhesive material layer may be disposed. The hook material has many engaging projections on a connecting surface thereof. Examples of the shapes of the engaging projections include a tick shape, a J shape, a mushroom shape, a T shape, and a double J shape (a shape in which the J-shaped ones are connected to each other back to back), but any shape may be used.

The connecting portion 13A can be attached directly to the back wing 81, or as shown in the illustrated example, a connecting tape 13 having the connecting portion 13A can be attached to the back wing 81. The structure of the connecting tape 13 is not particularly limited. However, in the illustrated example, the connecting tape 13 includes: a tape attachment portion 13C fixed to the side flap part SF; a tape main unit portion 13B protruding from the tape attachment portion 13C; and a connecting portion 13A disposed in an intermediate portion of the tape main unit portion 13B in the width direction, and a tip side of the connecting portion 13A is a tab part. As a sheet material composed of the tape attachment portion 13C and the tape main unit portion 13B, a nonwoven fabric, a plastic film, a polyethylene laminated nonwoven fabric, paper, or a composite material thereof can be used.

A connected part for the connecting portion 13A on the outer surface of the ventral side portion F can be appropriately determined, and only a main portion disposed between the front wing 80 on the right side and the front wing 80 on the left side may be used as the connected part, or a range from a side portion of the main portion to a portion of each front wing 80 at the base end portion side thereof may be used as the connected part. Each of these connected parts preferably enables easy connection of the connecting portion 13A thereto. For example, in a case where the connecting portion 13A is composed of a hook material (male member) of a mechanical fastener (hook and loop fastener), the connected part on the outer surface of the ventral side portion F may be composed of a loop material (female member) or may be a nonwoven fabric. A loop material which is formed by sewing loop yarns to a plastic film is known, but it is preferable that a loop material is formed by disposing welded portions of fibers welded each other intermittently at least in the width direction WD on a long fiber nonwoven fabric (such as a spunbond nonwoven fabric having the fineness of about 2.0 to 4.0 dtex, the basis weight of about 20 to 50 $g/m^2$, the thickness of about 0.3 to 0.5 mm) having the fiber continuous direction being the width direction WD, from the view point of air permeability and flexibility. As in the illustrated example, in a case where a region including the connected part on the outer surface of the ventral side portion F is formed with the exterior nonwoven fabric 12, the hook material can be connected to the exterior nonwoven fabric 12 without adding any means. As desired, the loop material may be attached only to the connected part on the outer surface of the ventral side portion F. In addition, in a case where the connecting portion 13A is the adhesive material layer, it is possible to attach a plastic film having a smooth surface with high pressure-sensitive adhesiveness to the connected part on the outer surface of the ventral side portion F.

(Fixing of Top Sheet)

The top sheet 30 is preferably bonded to a back surface side member located at a back surface side of the top sheet 30 with a hydrophobic hot melt adhesive 31. As long as a fixing portion of the top sheet 30 extends at least over the entire hole-arranging area, the fixing portion may extend beyond this area (for example, over the entire top sheet 30) or may extend only in the hole-arranging area. The intermediate sheet 40, the wrapping sheet 58, and the liquid impervious sheet 11 may be referred to as the back surface side member in the illustrated example, but the back surface side member is not limited thereto.

Examples of the hydrophobic hot melt adhesive 31 can include an EVA-based agent, a polyolefin-based agent, and a polyester/polyamide-based agent, particularly a pressure sensitive adhesive rubber-based agent (elastomer-based agent) can be used preferably.

The application amount of the hydrophobic hot melt adhesive 31 can be determined appropriately, but it can be about 0.1 to 10 $g/m^2$. Particularly it is preferable that the application amount of the hydrophobic hot melt adhesive 31 is 0.5 to 5 $g/m^2$, because the hot melt adhesive 31 having such application amount may be prevented from overflowing the hole 14. Even so, since the adhesion of the hot melt adhesive is likely to be inhibited by the skin care liquid described later, it is desirable that also the application pattern of the skin care liquid is considered simultaneously. The application pattern of the hydrophobic hot melt adhesive 31 can be determined appropriately, but a delicate application pattern in which small portions having no applied hot melt adhesive are scattered (such as a spray application into a spiral shape, a Z shape, or a wave shape) is preferable, and a continuous surface shaped application pattern such as a slot application is also preferable.

(Liquid-Containing Area)

The skin-contacting region of the top sheet 30 has, as illustrated in FIGS. 7, 10 and 11, the liquid-containing area 32 containing the hydrophilic skin care liquid, and the overlapping area 33 in which the liquid-containing area 32 and the hole-arranging area are overlapped each other. In a case where an oil-soluble skin care liquid is used, when the skin care liquid comes into contact with the hydrophobic hot melt adhesive 31 in the overlapping area 33, adhesion with the hot melt adhesive 31 is likely to be inhibited (and such inhibition includes reducing of bonding force and thereby includes interfacial peeling, in addition, includes also failure in bonding). On the other hand, in a case where the hydrophilic skin care liquid is used, when the skin care liquid comes into contact with the hydrophobic hot melt adhesive 31 in the overlapping area 33, the adhesion with the hot melt adhesive 31 is less likely to be inhibited. As a result, this makes it less likely that the top sheet 30 is partly peeled off from the back surface side member. Thus, the corruption of the holes 14 and the formation of the wrinkles, which would be caused in the peeled part of the top sheet 30, can be prevented, the visibility of the holes 14 is therefore not less likely to be deteriorated.

As long as the skin-contacting region has the overlapping area 33 in which the liquid-containing area 32 and the hole-arranging area are overlapped each other, the entire part of the liquid-containing area 32 may be the overlapping area 33, and only a part of the liquid-containing area 32 may be the overlapping area 33. For example, in a case where the hole-arranging area is disposed over the entire top sheet 30, in the illustrated example, the entire liquid-containing area 32 corresponds to the overlapping area 33 located in the hole-arranging area. That is, the arrangement of the liquid-containing area 32 is not limited as long as the skin-contacting region has the overlapping area 33 in which the liquid-containing area 32 and the hole-arranging area are overlapped each other, and can be determined in consideration of skin care effects and the used amount thereof. For example, concerning the skin care effects for the crotch portion, the liquid-containing area 32 can be disposed only in an intermediate part in the front-back direction LD of the top sheet 30 as illustrated in FIG. 10. It is needless to say that as illustrated in FIG. 11, the liquid-containing area 32 can be disposed so as to be continuous throughout in the front-back direction LD of the top sheet 30. In this case, it is possible to make the contained amount of the skin care liquid in a first area 32*a* located at an intermediate part in the front-back direction LD larger than those in second areas 32*b* located at a front side and at a back side of the first area 32*a*.

The contained amount of the skin care liquid may be appropriately determined. As one example, it is preferable that the liquid-containing area has a portion in which 5 to 15 $g/m^2$ of the hydrophilic skin care liquid per unit area is contained. As in an example illustrated in FIG. 11, in a case where the liquid-containing area 32 has two or more areas having different contained amounts of the skin care liquid, or in a case where the application amount of the skin care liquid is changed continuously, it is preferable that the contained amount of the skin care liquid is 2 to 20 $g/m^2$ as the entire liquid-containing area 32; the rate of area of a portion in which 5 to 15 $g/m^2$ of the skin care liquid is contained to the area of the liquid-containing area 32 is 20% or more; or both the above two conditions are satisfied.

The component composition of the hydrophilic skin care liquid is not particularly limited, and examples thereof may include glycerin, propylene glycol, dipropylene glycol, 1,3-butylene glycol, polyethylene glycol, sorbitol, xylitol, and sodium pyrrolidone carboxylate, further, as a main component, one kind or two or more kinds of saccharides such as trehalose, mucopolysaccharides (e.g., hyaluronic acid and the derivatives thereof, chondroitin and the derivatives thereof, heparin and the derivatives thereof, etc.), elastin and the derivatives thereof, collagen and the derivatives thereof, NMF-related substances, lactic acid, urea, ester of octyldodecyl and higher fatty acids, extract of seaweed, extract of *Bletilla striata* (hyacinth orchid) root, various kind of amino acids and derivatives thereof, but a moisturizing agent containing glycerin as a main component is preferable. The moisturizing agent containing the glycerin as the main component contains 70% by mass or more of glycerin as a component composition, and if necessary, one or more kinds additives selected from the group of emulsifier, phosphate ester, paraffin and surfactant are contained. Preferable surfactant is nonionic surfactant including an ether type nonionic surfactant and an EO-PO type nonionic surfactant.

The positional relation between the liquid-containing area 32 and the pattern of the holes 14 can be appropriately determined. For example, in the illustrated example, in the pattern of the holes 14, rows 95 of the holes 14 aligned at intervals in the front-back direction LD are arranged at intervals in the width direction WD. In such a case, it is preferable that the skin care liquid is applied in a stripe state (the liquid-containing area 32 is formed in a stripe state) along the front-back direction LD, an application width 32W of the skin care liquid is twice or less of a maximum value 14d of a center-to-center interval of two holes 14 of two rows 95 of the holes 14 adjacent to each other in the width direction WD, and an application interval 32X of the skin care liquid is twice or more of the maximum value of the center-to-center interval of the two holes 14 of the two rows 95 of the holes 14 adjacent to each other in the width direction WD. That is, even if the combination of the hydrophilic skin care liquid and the hydrophobic hot melt adhesive is adopted, this does not make possible to prevent completely the inhibition of the adhesion of the hot melt adhesive 31. For example, in a case where the hydrophilic skin care liquid is applied to the top sheet 30 and after that, the top sheet 30 is bonded to the back surface side member with the hydrophobic hot melt adhesive 31, the adhesion of the hot melt adhesive 31 is inhibited to some extent. Therefore, when the arrangement of the liquid-containing area 32 has the above positional relation with respect to the pattern of the holes 14, even if the adhesion of the hot melt adhesive 31 is inhibited such that the top sheet is partly peeled off, the number of the holes 14 whose visibility might be deteriorated can be small, which is preferable.

In the examples illustrated in FIGS. 6(*f*), 7 and 8, groups 90 of the holes 14 arranged in single-wavy lines or chained lines continuous in the front-back direction LD are arranged at intervals in the width direction WD (in a form of repeated unit arrangement portions 94) such that two groups 90 of the holes adjacent to each other in the width direction WD are arranged in a same phase or different phases in the front-back direction LD. In such a case, it is preferable that the skin care liquid is applied in a stripe state, an application width of the skin care liquid is one-third or less of a width 94W of a unit arrangement portion 94 in a group 90 of the holes 14, and an application interval of the skin care liquid is one-third or more of the width 94W of the unit arrangement portion 94 in the group 90 of the holes 14. When the arrangement of the skin care liquid has the above positional relation with respect to the pattern of the holes 14, even if the adhesion of the hot melt adhesive 31 is inhibited such that the top sheet is partly peeled off, since this occurs only in a part of the unit arrangement portion 94, there is less likely to deteriorate visibility of the whole pattern, which is preferable.

<Description of Terms Used in Specification>

The following terms used in the specification should be understood to have the meanings defined below unless otherwise specified in the specification.

"Front-back direction" means a direction (longitudinal direction) indicated by a reference sign LD in the drawings, "width direction" means a direction (left-right direction) indicated by a reference sign WD in the drawings, and the front-back direction and the width direction are orthogonal to each other.

"Machine direction (MD)" and "cross direction(CD)" mean the flow direction (MD) in a manufacturing equipment and the lateral direction (CD) orthogonal to the flow direction, and either one is the front-back direction and the other is the width direction of a product depending on a component of the product. The MD of a nonwoven fabric is the direction of fiber orientation of the nonwoven fabric. The fiber orientation is a direction along which a fiber of a nonwoven fabric runs and can be determined by, for example, a measurement method in accordance with the fiber orientation test method based on the zero distance tensile strength of TAPPI standard method T481 or a simple measurement method for determining the fiber orientation direction from the tensile strength ratio of the front-back direction and the width direction.

"Front surface side" means a side closer to a wearer's skin when a disposable diaper is worn, and "back surface side" means a side far from a wearer's skin when a disposable diaper is worn.

"Front surface" means a surface of a portion closer to a wearer's skin when a disposable diaper is worn, and "back surface" means a surface of a portion far from a wearer's skin when a disposable diaper is worn.

"Area rate" means a rate of a target portion to a unit area and is expressed as a percentage obtained by dividing a total area of target portions (for example, the holes) in a target region (for example, a cover nonwoven fabric) by an area of the target region. In a mode in which a large number of the target portions are provided at intervals, it is desirable to set the size of the target region such that ten or more target portions are included therein and obtain the area rate. For example, the area rate of the holes can be measured by the following procedure, for example, using the trade name VHX-1000 manufactured by KEYENCE CORPORATION under a measurement condition of magnification of ×20.

(1) Set a lens to with a magnification of ×20 and adjust a focus. Adjust the position of a nonwoven fabric such that 4 holes×6 holes come in sight.

(2) Specify the brightness of "hole" and measure the area of the hole.

(3) Click extraction color of [Area Measurements] in [Measurement/Comment]. Click "hole".

(4) Click [Block Measurement], check [Displaying the measurement result window] and save the measurement result as CSV data.

"Stretch rate" means a value obtained when a natural length is 100%. For example, a stretch rate of 200% is synonymous with an elongation ratio of 2.

"Gel strength" is measured as follows: 1.0 g of super absorbent polymers is added to 49.0 g of artificial urine (urea: 2 wt %, sodium chloride: 0.8 wt %, calcium chloride dihydrate: 0.03 wt %, magnesium sulfate heptahydrate: 0.08 wt %, and ion exchanged water: 97.09 wt %) and the mixture is agitated with a stirrer. The resulting gel is left in a thermo-hygrostat at 40° C.×60% RH for three hours and then cooled to room temperature. The gel strength of the gel is measured with a curdmeter (Curdmeter-MAX ME-500 manufactured by I. Techno Engineering Co., Ltd).

"Basis weight" is measured as follows. After preliminary drying of a sample or a test piece, the sample or the test piece is left in a test room or a test device under normal conditions (an ambient temperature of 23±1° C. and with a relative humidity of 50±2% at the testing site) until the weight of sample or test piece reaches constant mass. Preliminary drying is to achieve the constant mass of the sample or test piece under an environment having a temperature of 100° C. For fibers having a standard moisture regain of 0.0%, preliminary drying may be omitted. The test piece having the constant mass is cut with a cutting template having the size of 100 mm×100 mm into samples having the size of 100 mm×100 mm. The weight of the sample is measured. The measured weight is multiplied by 100 to determine the weight per one square meter, which is defined as the basis weight.

"Thickness" is automatically measured under the conditions that a load is 0.098 N/cm$^2$ and a pressing area is 2 cm$^2$ using an automatic thickness measuring device (KES-G5 handy compression measurement program). The thickness of the perforated nonwoven fabric is measured at sites other than the holes and the protruding portions formed at surroundings thereof.

Water absorption capacity is measured in accordance with JIS K7223-1996 "Testing method for water absorption capacity of super absorbent polymers."

Water absorption rate is defined as "time that elapse before the end point" measured with 2 g of super absorbent polymers and 50 g of normal saline solution in accordance with JIS K7224-1996 "Testing method for water absorption rate of super absorbent polymers."

"Spread state" means a flatly spread state without contraction or slack.

The dimensions of the components are measured in a spread state, not the natural length state, unless otherwise specified.

"Melt viscosity" is measured in accordance with JIS Z 8803 at a specified temperature, using Brookfield Viscometer with Spindle No. 027.

"Maximum dimension" of the hole is the dimension in MD or the dimension in CD, whichever is longer.

The tests and measurements are carried out in a test room or a test device under normal conditions (an ambient temperature of 23±1° C. and with a relative humidity of 50±2% at the testing site), unless the environmental condition for the tests and measurements are otherwise specified.

INDUSTRIAL APPLICABILITY

The present invention is applicable to overall disposable diapers such as pad-type disposable diapers, disposable swimsuits, diaper covers, sanitary napkins and the like in addition to underpants-type disposable diapers and tape-type disposable diapers.

REFERENCE SIGNS LIST 11 liquid impervious sheet
14 hole
14e protruding portion
20 exterior nonwoven fabric
30 top sheet
40 intermediate sheet
50 absorbent element
56 absorber
58 wrapping sheet
60 rising gather
62 gather sheet
LD front-back direction
WD width direction
90 group
93 hole-less portion
31 hydrophobic hot melt adhesive
32 liquid-containing area
33 overlapping area
94 unit arrangement portion

The invention claimed is:

1. A disposable wearing article comprising
a top sheet including a skin-contacting region which is in contact with skin of a wearer, wherein
the top sheet is formed of a perforated nonwoven fabric having a hole-arranging area in which holes penetrating the perforated nonwoven fabric from a front surface thereof to a back surface thereof are arranged in a predetermined pattern,
the skin-contacting region has a liquid-containing area containing a hydrophilic skin care liquid, the hole-arranging area, and an overlapping area in which the liquid-containing area and the hole-arranging area are overlapped each other, and
the top sheet is, at least at the entire hole-arranging area of the top sheet, bonded to a back surface side member located at a back surface side of the top sheet with a hydrophobic hot melt adhesive;
wherein the hydrophilic skin care liquid is in a liquid state at an ambient room temperature of approximately 23° C.

2. The disposable wearing article according to claim 1, wherein
the perforated nonwoven fabric has a fineness of 1 to 5 dtex and a basis weight of 10 to 30 g/m2,
the hydrophilic skin care liquid is a moisturizing agent containing glycerin as a main component,
the liquid-containing area has a portion in which 5 to 15 g/m2 of the hydrophilic skin care liquid per unit area is contained, and
an application amount of the hydrophobic hot melt adhesive is 0.1 to 10 g/m2.

3. The disposable wearing article according to claim 1, wherein
a maximum dimension of each of the holes is 0.5 to 2 mm and an area rate of the holes in the hole-arranging area is 0.1 to 10%.

4. The disposable wearing article according to claim 1, wherein
in the pattern, rows of the holes aligned at intervals in a front-back direction are arranged at intervals in a width direction,
the skin care liquid is applied in a stripe state,
an application width of the skin care liquid is twice or less of a maximum value of a center-to-center interval of two rows of the holes adjacent to each other in the width direction, and
an application interval of the skin care liquid is twice or more of the maximum value of the center-to-center interval of the two rows of the holes adjacent to each other in the width direction.

5. The disposable wearing article according to claim 1, wherein
in the pattern, groups of the holes arranged in single-wavy lines or chained lines continuous in a front-back direction are arranged at intervals in a width direction,
two groups of the holes adjacent to each other in the width direction are arranged in a same phase or different phases in the front-back direction,
the skin care liquid is applied in a stripe state,
an application width of the skin care liquid is one-third or less of a width of a unit arrangement portion in a group of the holes, and
an application interval of the skin care liquid is one-third or more of the width of the unit arrangement portion in the group of the holes.

6. The disposable wearing article according to claim 5, wherein the pattern is a Moroccan pattern.

7. The disposable wearing article according to claim 2, wherein
a maximum dimension of each of the holes is 0.5 to 2 mm and an area rate of the holes in the hole-arranging area is 0.1 to 10%.

8. The disposable wearing article according to claim 2, wherein
in the pattern, rows of the holes aligned at intervals in a front-back direction are arranged at intervals in a width direction,
the skin care liquid is applied in a stripe state,
an application width of the skin care liquid is twice or less of a maximum value of a center-to-center interval of two rows of the holes adjacent to each other in the width direction, and
an application interval of the skin care liquid is twice or more of the maximum value of the center-to-center interval of the two rows of the holes adjacent to each other in the width direction.

9. The disposable wearing article according to claim 3, wherein
in the pattern, rows of the holes aligned at intervals in a front-back direction are arranged at intervals in a width direction,
the skin care liquid is applied in a stripe state,
an application width of the skin care liquid is twice or less of a maximum value of a center-to-center interval of two rows of the holes adjacent to each other in the width direction, and
an application interval of the skin care liquid is twice or more of the maximum value of the center-to-center interval of the two rows of the holes adjacent to each other in the width direction.

10. The disposable wearing article according to claim 2, wherein
in the pattern, groups of the holes arranged in single-wavy lines or chained lines continuous in a front-back direction are arranged at intervals in a width direction,
two groups of the holes adjacent to each other in the width direction are arranged in a same phase or different phases in the front-back direction,
the skin care liquid is applied in a stripe state,
an application width of the skin care liquid is one-third or less of a width of a unit arrangement portion in a group of the holes, and
an application interval of the skin care liquid is one-third or more of the width of the unit arrangement portion in the group of the holes.

11. The disposable wearing article according to claim 3, wherein
in the pattern, groups of the holes arranged in single-wavy lines or chained lines continuous in a front-back direction are arranged at intervals in a width direction,
two groups of the holes adjacent to each other in the width direction are arranged in a same phase or different phases in the front-back direction,
the skin care liquid is applied in a stripe state,
an application width of the skin care liquid is one-third or less of a width of a unit arrangement portion in a group of the holes, and
an application interval of the skin care liquid is one-third or more of the width of the unit arrangement portion in the group of the holes.

12. The disposable wearing article according to claim 4, wherein
in the pattern, groups of the holes arranged in single-wavy lines or chained lines continuous in a front-back direction are arranged at intervals in a width direction,
two groups of the holes adjacent to each other in the width direction are arranged in a same phase or different phases in the front-back direction,
the skin care liquid is applied in a stripe state,
an application width of the skin care liquid is one-third or less of a width of a unit arrangement portion in a group of the holes, and
an application interval of the skin care liquid is one-third or more of the width of the unit arrangement portion in the group of the holes.

13. The disposable wearing article according to claim 1, wherein the liquid-containing area is continuous throughout in a front-back direction of the top sheet, and
in the liquid-containing area, a contained amount of the skin care liquid in a first area located at an intermediate part in the front-back direction is larger than a contained amount of the skin care liquid in second areas located respectively at a front side and at a back side of the first area.

\* \* \* \* \*